United States Patent
Lumbantobing et al.

(10) Patent No.: US 8,314,586 B2
(45) Date of Patent: Nov. 20, 2012

(54) SYSTEM FOR ADAPTING THE RESONANT OPERATION OF A PERSONAL CARE APPLIANCE DURING THE LIFETIME THEREOF

(75) Inventors: Ari Lumbantobing, Issaquah, WA (US); Kevin Miller, Bellevue, WA (US); Meindert Norg, Canonsburg, PA (US); Pieter Johannes Bax, Drachten (NL)

(73) Assignee: Koninklijke Philipes Electronics N.V., Eindhoven (NL)

( * ) Notice: Subject to any disclaimer, the term of this patent is extended or adjusted under 35 U.S.C. 154(b) by 682 days.

(21) Appl. No.: 12/446,780

(22) PCT Filed: Oct. 31, 2007

(86) PCT No.: PCT/IB2007/054424
§ 371 (c)(1),
(2), (4) Date: Oct. 13, 2009

(87) PCT Pub. No.: WO2008/053441
PCT Pub. Date: May 8, 2008

(65) Prior Publication Data
US 2010/0109580 A1    May 6, 2010

Related U.S. Application Data

(60) Provisional application No. 60/856,389, filed on Oct. 31, 2006.

(51) Int. Cl.
*H02P 3/18*    (2006.01)
*H02H 7/08*    (2006.01)

(52) U.S. Cl. .............. 318/807; 318/738; 318/254.1; 318/244; 318/400.32; 318/400.34; 318/400.35

(58) Field of Classification Search .............. 318/807, 318/738, 254.1, 244, 400.32, 400.34, 400.35
See application file for complete search history.

(56) References Cited

U.S. PATENT DOCUMENTS

| | | | |
|---|---|---|---|
| 5,613,259 A * | 3/1997 | Craft et al. ............... | 15/22.1 |
| 6,437,524 B1 | 8/2002 | Dimanstein | |
| 2003/0233877 A1 | 12/2003 | Grez et al. | |
| 2004/0008105 A1 | 1/2004 | Rota et al. | |
| 2006/0144173 A1 | 7/2006 | Taghezout | |

FOREIGN PATENT DOCUMENTS

| | | |
|---|---|---|
| DE | 102004029684 A1 | 12/2005 |
| JP | 2003210492 | 7/2003 |
| JP | 2006016142 A | 1/2006 |
| WO | 2005058188 A1 | 6/2005 |
| WO | 2006003617 A1 | 1/2006 |
| WO | 2007072365 A1 | 6/2007 |

* cited by examiner

*Primary Examiner* — Walter Benson
*Assistant Examiner* — Erick Glass

(57) ABSTRACT

The adapting system for a resonant drive appliance includes a circuit for measuring the back EMF induced in the stator coil of the motor following turn-off of the appliance. The frequency of the back EMF signal is determined from the zero crossings of the EMF signal. The determined frequency is then compared with a running average of previous frequency determinations, and the drive frequency of the appliance is adjusted if the difference between the compared frequencies is greater than a threshold value, e.g. 1 Hz.

13 Claims, 5 Drawing Sheets

SYSTEM FOR ADAPTING THE RESONANT OPERATION OF A PERSONAL CARE APPLIANCE DURING THE LIFETIME THEREOF

This invention relates generally to resonant-driven small appliances, such as a personal care appliance, and more specifically concerns a system for adapting the operation of such an appliance during the lifetime thereof.

In a resonant drive system, such as may be used to drive a small appliance, for example, a power toothbrush, the natural resonant frequency of the appliance is an important consideration relative to the efficient operation of the appliance. When such an appliance is excited, it responds best at its natural resonant frequency, i.e. providing the greatest output for a given input. For maximum efficiency, the drive frequency of the motor that produces the operating action is selected to be at or near the natural frequency of the appliance, e.g. the drive frequency is a few Hz below the natural frequency of the device.

However, during the lifetime of operation of such devices, the change in the natural resonant frequency of the device, such as due to normal wear and tear of the parts, results typically in a decrease in performance because of the resulting mismatch between the drive frequency and the natural resonant frequency of the appliance. Up to the present, there has been no way to correct for this change in the natural frequency of the appliance over time and hence, the decrease in performance of such devices goes uncorrected during their lifetime and the beneficial results degrade, leading to customer dissatisfaction or early disposal of the appliance.

Hence, it would be desirable to be able to adapt the operation of the appliance during its lifetime to maintain consistent efficient performance over an extended period of time.

Accordingly, the embodiment described herein is a system provided within an appliance having a resonant drive system for adapting the operation of said appliance during the lifetime of the appliance, comprising: an appliance having a resonant drive system which includes a motor assembly having a stator coil; a circuit for measuring back EMF induced in the stator coil by an operating portion of the appliance after the appliance has been turned off; a system for determining the natural resonant frequency of the appliance from the back EMF; a comparator for comparing said determined natural resonant frequency with a known appliance frequency indicative of the natural resonant frequency; and an adjusting circuit for changing the drive frequency of the appliance if the difference between the determined frequency and the known natural frequency of the appliance is greater than a predetermined amount.

The embodiment also includes a corresponding method for adapting the operation of an appliance.

Figure 1:
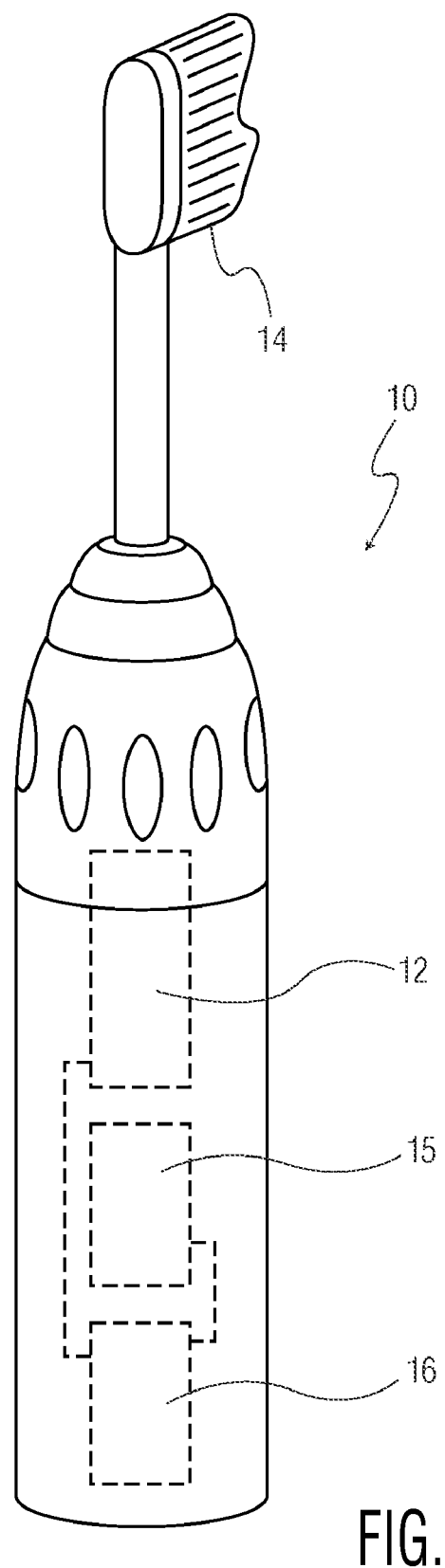
FIG. 1 is a perspective view showing an example of a personal care appliance and the major parts of a resonant drive system therefor.

FIG. 1 shows an example of a small appliance with a resonant dynamic drive system. Specifically, the appliance, shown generally at 10, is a power toothbrush. However, it should be understood that other appliances which have a resonant drive can include the system of the present invention. Examples of such appliances include skin brushes, shavers and similar devices. Power toothbrush 10 includes a drive motor 12, which drives a workpiece 14 with a desired action at a drive frequency which is equal to or near the natural resonant frequency of the appliance. An example of such an appliance is shown in U.S. Pat. No. 5,189,751, which is owned by the assignee of the present invention, the contents of which are hereby incorporated by reference.

Drive motor 12 is responsive to a drive control circuit 15 which includes a microprocessor with a software program and produces a motor drive signal with the drive frequency. The motor is powered by batteries 16 which can be either replaceable or rechargeable, in which case the appliance is used with a separate charging device (not shown).

In the embodiment shown and described, the natural resonant frequency (natural frequency) of the appliance as a whole is periodically determined during its operating lifetime, typically every time the device is used and then powered off. This natural frequency value is then compared with a standard value, which typically is updated along with the updating of the drive frequency. If the difference between the two is larger than a preselected threshold, the drive frequency of the drive signal produced by the drive control circuit, or similar drive system, is changed to maintain the original relationship between the natural frequency and the drive frequency.

In the example discussed above, the drive frequency will thus remain equal to or near (within a few Hz) the natural frequency of the appliance. This arrangement thus adapts the operation of the appliance periodically during the operating lifetime of the appliance, maintaining the performance of the appliance at a desired high level and compensating for typical wear and tear of the device, as well as any other factors which would result in a change in the natural resonant frequency of the appliance.

Figure 2:
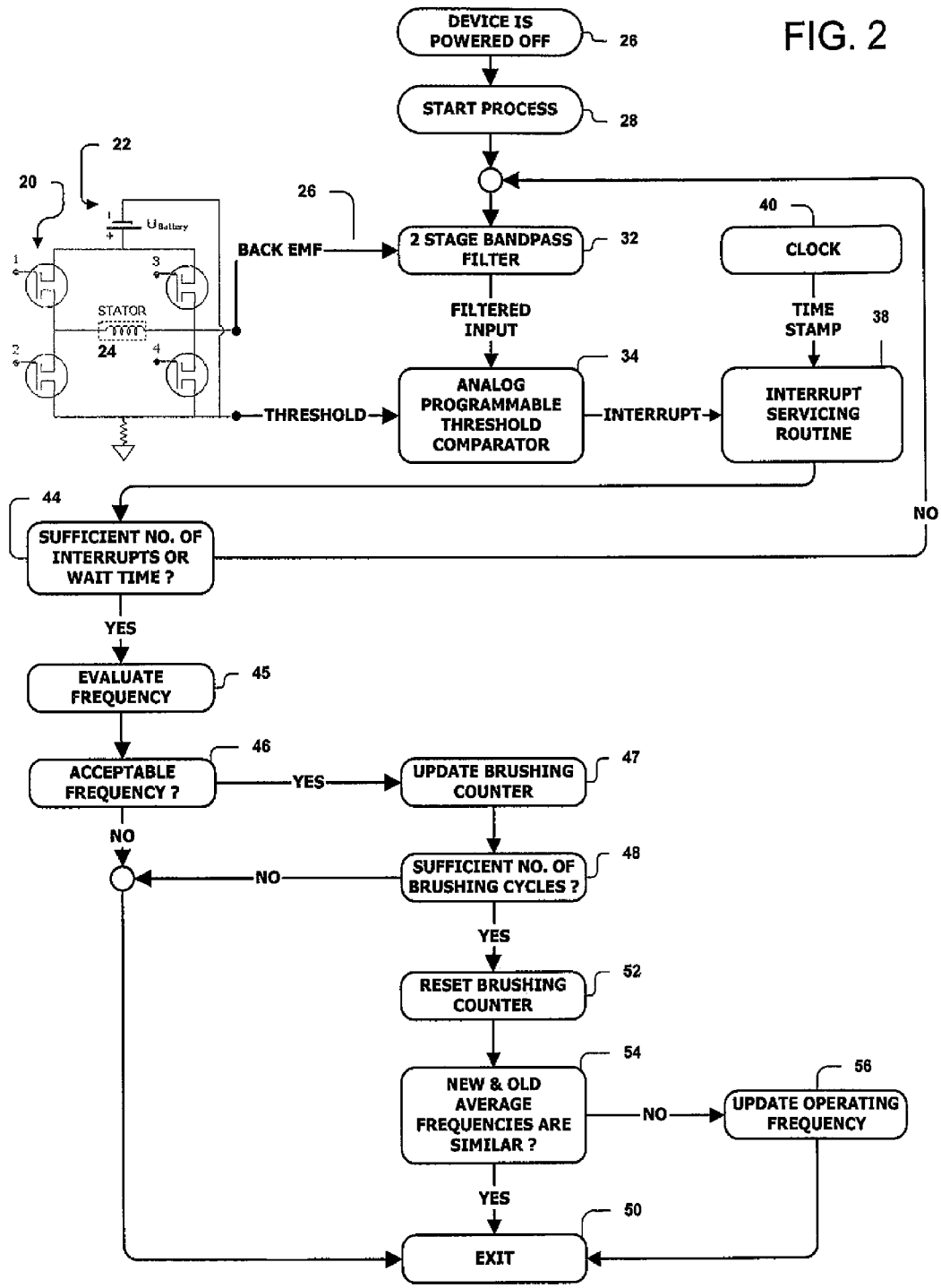
FIG. 2 is a block diagram of the system of the present invention, capable of adapting the operation of the resonant drive system during the lifetime of the appliance.

This system is shown in one implementation in software in FIG. 2. An appliance motor with its electronic controls (one example) is shown at 20, powered by a battery 22. The motor circuit 20 includes a stator coil 24. When the device is powered off, as shown at software functional block 26, such as following a typical brushing event, the adaption process is initiated, as shown at block 28. In the embodiment shown, the natural resonant frequency is determined by first obtaining the value of back EMF (voltage) which is induced in the stator coil by the residual action of the vibrating member on which the workpiece is mounted, which occurs following turn-off of the device. In the device in the '751 patent for instance, the residual movement of the drive arm, on the back end of which are mounted permanent magnets, induces a back EMF into the stator coil in the electromagnetic motor.

The back EMF, shown on line 26, is applied to a two-stage band pass filter 32, the output of which is applied to one input of a programmable comparator 34. Applied to the other input of comparator 34 is a threshold voltage, or a ground connection. When the filtered input signal crosses the value of the threshold signal (or ground), as determined by the programmable comparator 34, an interrupt occurs which is applied to the interrupt routine 38 which is part of the software program in the microprocessor. This interrupt (zero crossing) occurs for example approximately 20 times following the device being turned off. The zero crossings are processed, using a clock signal 40 to mark the zero crossings, producing the times between successive zero crossings.

It should be understood that there are other ways to detect the time between zero crossings than by using an interrupt and a microprocessor, such as an analog timer with associated comparators or by multiplying the back EMF signal with a known sine-signal of the expected frequency and then measuring the zero crossings of the result.

The number of zero crossings (interrupts in this embodiment) for a brushing event is accumulated and applied to processing block 44, which determines whether or not there have been a sufficient number of interrupts (zero crossings) to produce a reliable frequency determination. Typically, 10 will be the minimum, although in some cases it can be fewer, particularly if the first few (e.g. 4) are ignored for accuracy, while any number in the range of 10-20 is acceptable. If there is a sufficient number of interrupts, the frequency evaluation is started. If there is not the minimum number of interrupts, the program exits back to wait for the next brushing event. Typically in the frequency evaluation as shown at block 45, the first four zero crossings are ignored, as indicated above. This is to ensure that the portion of the back EMF signal used for frequency determination is not affected by the dynamics of the drive circuit. The drive circuit may require a settling time following the device being turned off, e.g. <0.1 seconds, which is approximately equal to the period of four zero crossings. A frequency determination, as shown in block 45, is then performed using the remaining zero crossings. If the determined frequency falls outside an acceptable window, as shown in block 46, e.g. ±10 Hz relative to a previous determined frequency average, the program will exit and wait for the next brushing event.

If the program continues, the brushing counter is updated at block 47 and an inquiry is then made at block 48 as to whether there has been a sufficient number of previous brushing cycles which have resulted in frequency determinations in order to provide a reliable frequency comparison, as explained below. If there has not, the program is exits at 50. If there has been a sufficient number of brushing cycles, the brushing counter is re-set at 52 and the present frequency, determined at 46, is evaluated at block 54 against a running average of previously determined frequencies. For example, this average could be in the range of 200 Hz-280 Hz in a particular appliance, although this could vary, depending on the particular appliance. In the embodiment shown, the last 20 brushing frequency determinations are used for the running average. This number could vary, however.

If the new frequency and the running average frequency are similar within a specific range, then the program is exited at 50 to wait for the next determination, typically the end of the next brushing. If the frequencies are not similar, then the drive frequency of the device is updated, at block 56. In the embodiment shown, the dissimilarity must be at least 1 Hz in order to update the drive frequency, although this can be varied to make the device more or less sensitive to resonant frequency change.

Figure 3A:
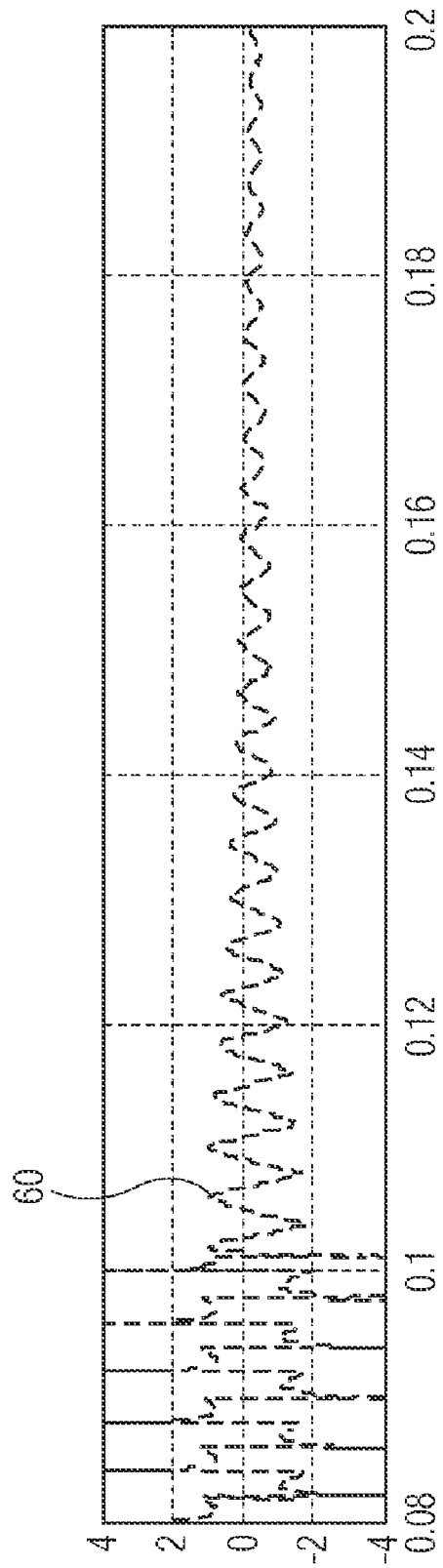
FIGS. 3A and 3B are signal diagrams illustrating the operation of the system of FIG. 2.
Figure 3B:
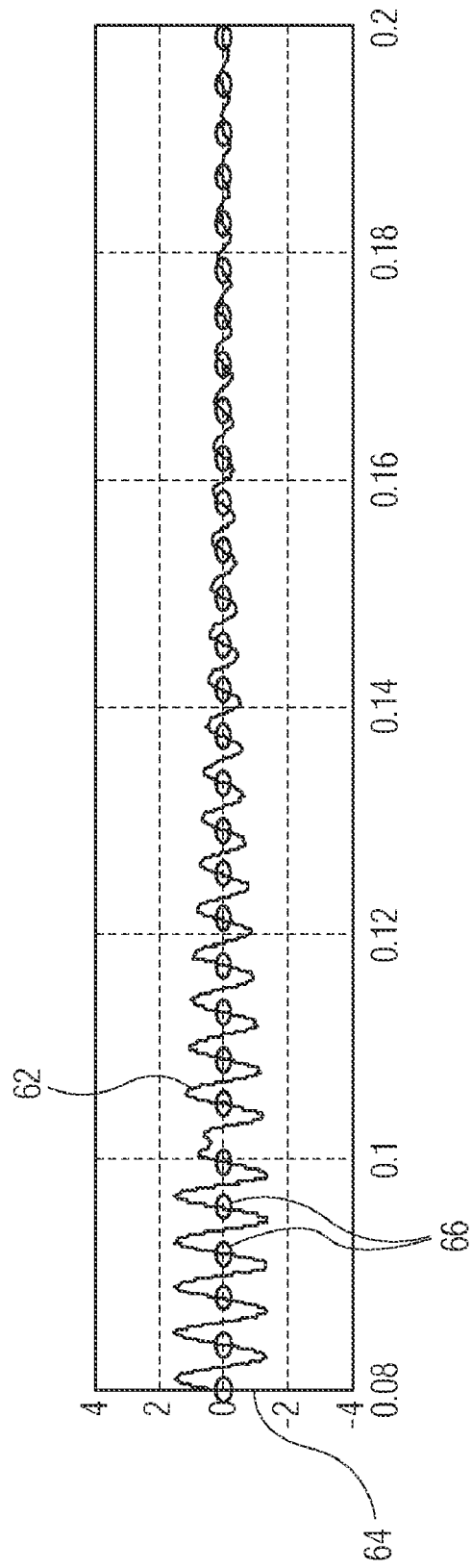

FIG. 3A shows the raw signal data 60 (back EMF in volts) as it rings down from shut-off of the device for approximately 0.2 seconds, at which point it has decreased close to zero. FIG. 3B shows the adjusted back EMF 62, in which the average value of the voltage has been removed, such that the ringing is centered on the zero line 64. The circles 66 in FIG. 3B along the zero line indicate the actual zero crossings of the voltage.

As discussed above, the time difference between the zero crossings is determined by the processor, after marking by the clock, and the instantaneous estimated resonant frequency is then determined. Typically the ringing will occur for 5-20 cycles before reaching zero. The determined frequency as discussed above is then compared in the processor with the running average of a selected number of previous determined frequencies, again for example, the last 20 determined frequencies. A change is made to the drive frequency if the frequency difference is greater than a selected threshold amount. The use of back EMF to determine the natural resonant frequency has proven to provide accurate results and can be done with existing parts and the existing microprocessor in many power toothbrushes.

While the circuit of FIG. 2 shows that the back EMF on the stator coil is taken from one end of the stator coil, with the other end grounded, with a comparison then being made against a threshold voltage, the back EMF across the stator coil (differential voltage) can also be used. The differential voltage is then used for the voltage comparison.

Figure 4:
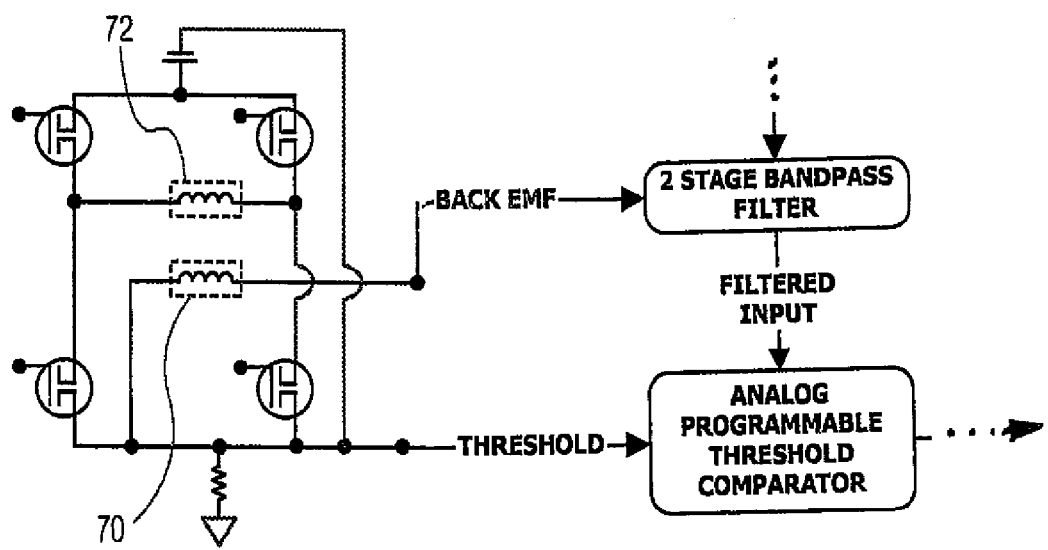
FIG. 4 is a partial block diagram of an alternative embodiment to the system of FIG. 2.

FIG. 4 shows a variation of the arrangement of FIG. 2, in which the back EMF is obtained from a separate sensing coil 70, as opposed to stator coil 72. This embodiment requires a separate additional coil in the device, adjacent to the stator coil and thus adds expense, but has the advantage of a clearer measurement (less noise) and an average signal of zero, which is helpful in detecting zero crossings. The sensing coil can be positioned close to the moving magnets, and the coil can also be used as a sensor for stabilizing the amplitude of the moving part of the actuator during operation of the device. The remainder of the circuit/process of the system of FIG. 4 is identical to the system of FIG. 2.

Hence, a system has been described which is used as part of a resonant drive system to adjust the drive frequency periodically during the lifetime of the appliance as the natural resonant frequency of the device changes due to normal wear and/or other factors.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. A resonant appliance which includes a system for adapting the operation of said appliance during a lifetime thereof, comprising:
    said appliance having a drive system, with a drive frequency, which includes a motor assembly having a stator coil;
    a circuit for measuring back EMF induced in the stator coil or a sensing coil separate from the stator coil after the appliance has been turned off;
    a system for periodically determining the natural resonant frequency of the appliance from the back EMF;
    a comparator for comparing said determined natural resonant frequency with a standard appliance frequency wherein the standard appliance frequency comprises a running average of a plurality of past determined natural resonant frequencies of the appliance; and
    an adjusting circuit for changing the drive frequency of the appliance if any difference between the determined natural resonant frequency and the standard frequency of the appliance is greater than a predetermined amount.

2. The system of claim 1, wherein the natural resonant frequency is determined by measuring a time period between successive crossings of the EMF signal relative to a reference value, and then determining the natural resonant frequency therefrom.

3. The system of claim 2, wherein the successive crossings comprise at least 10 crossings.

4. The system of claim 1, wherein the plurality of past frequencies are at least 20.

5. The system of claim 1, wherein the difference is at least 1 Hz.

6. The system of claim 1, wherein the back EMF used to determine the natural resonant frequency of the appliance is obtained from the stator coil.

7. The system of claim 1, wherein the back EMF is induced in a sensing coil separate from the stator coil.

8. A method for adapting operation of an appliance having a resonant drive system with a drive signal frequency, during a lifetime of the appliance, comprising the steps of:
  measuring back EMF induced into a coil within the device following the appliance being turned off wherein the back EMF has a frequency;
  determining the frequency of the back EMF, which is the natural resonant frequency of the appliance at that point;
  comparing said determined frequency with a pre-established reference frequency, wherein the reference frequency is a running average of a plurality of immediate past frequency determinations; and
  changing the drive signal frequency of the appliance if any difference between the determined frequency and the reference frequency is greater than a predetermined amount.

9. The method of claim 8, wherein the natural resonant frequency is determined by obtaining a time period between successive crossings of the EMF signal relative to a reference value, and then calculating the natural resonant frequency therefrom.

10. The method of claim 9, wherein there are at least 10 reference value crossings by the EMF signal, wherein the determined frequency is an average of the frequency determinations from the reference value crossings.

11. The method of claim 9, wherein the frequency difference is at least 1 Hz.

12. A resonant drive appliance which includes a system for adapting operation of said appliance during a lifetime thereof, comprising:
  an appliance having a resonant drive system which includes a motor assembly having a stator coil;
  means for measuring back EMF induced in the stator coil or a sensing coil separate from the stator coil after the appliance has been turned off;
  means for determining the natural resonant frequency of the appliance from the back EMF;
  a comparator for comparing said determined natural resonant frequency with a standard appliance frequency and comprising a running average of a plurality of past determined natural resonant frequencies; and
  means for changing a drive frequency of the appliance if the difference between the determined frequency and the standard appliance frequency is greater than a predetermined amount.

13. The system of claim 12, wherein the natural resonant frequency is determined by measuring a time period between successive crossings of the EMF signal relative to a reference value and then determining the natural resonant frequency therefrom.

* * * * *